(12) United States Patent
Shellenberger

(10) Patent No.: US 7,273,884 B2
(45) Date of Patent: Sep. 25, 2007

(54) METHOD OF TREATING TREMORS

(75) Inventor: M. Kent Shellenberger, Sequim, WA (US)

(73) Assignee: Eisai, Inc., Teaneck, NJ (US)

( * ) Notice: Subject to any disclaimer, the term of this patent is extended or adjusted under 35 U.S.C. 154(b) by 189 days.

(21) Appl. No.: 10/663,187

(22) Filed: Sep. 15, 2003

(65) Prior Publication Data

US 2004/0142992 A1 Jul. 22, 2004

Related U.S. Application Data

(60) Provisional application No. 60/410,399, filed on Sep. 13, 2002.

(51) Int. Cl.
*A61K 31/42* (2006.01)
(52) U.S. Cl. .................................................. 514/379
(58) Field of Classification Search ................. 514/379
See application file for complete search history.

(56) References Cited

U.S. PATENT DOCUMENTS

| 4,172,896 A | 10/1979 | Uno et al. |
| 4,981,867 A * | 1/1991 | Prince ........................ 514/423 |
| 6,342,515 B1 | 1/2002 | Masuda et al. |

FOREIGN PATENT DOCUMENTS

WO WO99/33465 * 7/1999

OTHER PUBLICATIONS

Moore et al., Journal of Physiology, 2000; 529(1):273-281.*
Kito et al., Seizure, 1996;5(2):115-119.*
Topaktas et al, Eur. Neurol., 27:114-119 (1987).
Murata et al, Neuroscience Research, 41:397-399 (2001).
Taira, No To Shinkei, 44(1):61-63 (1992) (Abstract).
Takigawa et al, Rinsho Shinkeigaku, 37(11):1006-1009 (1997) (Abstract).
Evidente, "Understanding Essential Tremor," Postgraduate Medicine, 108(5) (Oct. 2000).
We Move, "Clinical Characteristics of Essential Tremor," two pages, www.wemove.org/et/et_cc.html.
Wang et al, The Journal of Pharmacology and Experimental Therapeutics, 254:1006-1011 (1990).
Biary et al, Eur. Neurol., 35:217-219 (1995).
Racette et al, Stereotact Funct Neurosurg, 75:155-159 (2000).
Murata et al, J. Neurosurg., 99:708-715 (2003).
Taira, No To Shinkei, 44(1):61-63 (1992). (Complete Article in Japanese).
Taira, Brain and Nerve, 44(1):61-63 (1992). (English Language Translation of Complete Japanese Article).
Morita et al, Parkinsonism and Related Disorders, 11:101-103 (2005).
Zesiewicz et al, Movement Disorders, 22(2):279-282 (2007).
Zonegran (zonisamide) Package Insert, NDA 20-789, pp. 1-21 (2004).

* cited by examiner

*Primary Examiner*—San-Ming Hui
(74) *Attorney, Agent, or Firm*—Venable LLP

(57) ABSTRACT

The present invention is directed to a method of treating action tremor or severe essential tremor. Action tremor includes essential tremor, postural tremor, drug-induced or toxic tremor, primary orthostatic tremor, dystonic tremor, neuropathic tremor, and cerebellar tremor. The method comprises administering to a subject a pharmaceutical composition comprising an effective amount of zonisamide, or a pharmaceutically acceptable salt thereof. The methods of the present invention are useful in reducing symptoms of tremor. The compounds of the present method can also be used in conjunction with other therapeutic agents commonly used to treat tremor thus enhancing the therapeutic effect of treating tremor.

24 Claims, No Drawings

METHOD OF TREATING TREMORS

This application claims the benefit of U.S. Provisional Application No. 60/410,399, filed Sep. 13, 2002.

FIELD OF THE INVENTION

The present invention relates to methods of treating tremors, particularly essential tremor, with zonisamide (1,2-benzioxazole-3-methanesulfonamide).

BACKGROUND OF THE INVENTION

Tremor is defined as an involuntary, rhythmic oscillatory movement of a part or parts of the body, resulting from alternating or irregularly synchronous contractions of antagonist muscles. Tremor is the most common form of involuntary movement. Almost all individuals have experienced tremor at some point in their lives; however, only a small fraction of those with tremor seek medical attention. Tremors may result from normal (physiologic) or pathologic processes and may be characterized by their etiology or phenomenology (i.e., neuropathology, activation state, frequency, amplitude,). With the exception of those affecting the facial region, tremors are frequently defined or characterized by the joint around which the body part moves.

Tremor occurs when normal muscle activation is replaced by abnormal synchronous bursts. This evolves through alterations in ionic cell conductance in the cell membrane, causing the cell membrane to produce oscillation in its potential. The tendency to oscillate can be exaggerated by hyperpolarization of the cell away from the normal resting potential. Mainly, tremor is thought to be staged in the thalamic relay nuclei and inferior olive. The activity of neighboring cells can be coupled by electronic gap junctions in the olive and by recurrent axonal projections from the reticular nucleus in the thalamus. So, a large population of cells can oscillate together and exert a powerful rhythmic influence on motor output. Similarly, low-threshold calcium spike burst could be at the origin of rigidity and dystonia through the activation of the supplementary motor area and akinesia, when reaching the pre-supplementary motor area.

Individuals of all ages have tremor (physiological tremor) associated with anxiety, fatigue, anger, caffeine, pain, extreme cold, and other stressful situations. Excessive and persistent tremor is a neuro-pathologic phenomenon frequently associated with a neurological disorder called essential tremor. The National Institute of Neurological Disorders and Stroke estimates that as many as 10 million people in the United States are affected with essential tremor (ET). Essential tremor affects equally in females and males. Essential tremor may begin at any age, though it is unusual before the age of 20 years. Existing essential tremor often, though not always becomes worse with age, but may also make its initial appearance at an older age.

Pathologic tremor occurs when the normal continuous pattern of muscle activation is replaced by relatively synchronous neuronal bursting. This is characterized as an involuntary rhythmic oscillation of reciprocally innervated antagonistic muscle groups, causing movement of a body part about a fixed plane in space. Frequency of oscillation is divided into three main components: slow (3 to 5 Hz), intermediate (5 to 8 Hz), or rapid (9 to 12 Hz). The amplitude of oscillation is defined as fine, medium or coarse.

Current drug treatments of tremors do not offer long-term sustained efficacy and pose a high risk of complications with prolonged use. The most common and primarily prescribed treatment is a beta-blocker propranolol and its more potent, with longer half-life version, timolol. Many movement disorder specialists also choose to prescribe benzodiazepine (alprazolam, clonazepam, diazepam, lorazepam), anti-depressant (trazadone, mirtazapine), centrally acting alpha-agonist (clonidine), anti-apsamodic (botulinum toxin injection), anti-seizure (gabapentin, primidone, phenobarbital) type medications. It was recently reported that the noncompetitive NMDA channel blocker, MK-801 could block the tremorogenic actions of harmaline. Competitive blockade of harmaline-induced tremor by MK-801 occurs within the calcium channel coupled to the NMDA receptor.A number of surgical treatments have become available to these tremors. These procedures, which involve stimulation or ablation of the thalamic region via surgical intervention, have a risk factor of aneurysm and death of about 2 to 3%. Thus, there is a clear need for an effective, low risk therapy for tremors.

Zonisamide is an antiseizure drug classified as a sulfonamide and chemically unrelated to other antiseizure agents. Zonisamide has the chemical structure of 1,2-benzisoxazole-3-methanesulfonamide and is further characterized in the Merck Index (11$^{th}$ Ed. 1989) at monograph no. 10094. Zonisamide and related structures are described in described in U.S. Pat. No. 4,172,896, which is hereby incorporated herein by reference in its entirety for all purposes. It is approved for use in humans in the United States, Korea and in Japan. The mechanism(s) by which zonisamide exerts its antiseizure activity is unknown. Anticonvulsant activity has been demonstrated by an increase in threshold for generalized seizures in the kindled rat model and by a reduction in the duration of cortical focal seizures induced by electrical stimulation of the visual cortex in cats. Furthermore, zonisamide suppressed both interictal spikes and the secondarily generalized seizures produced by cortical application of tungstic acid gel in rats or by cortical freezing in cats.

Zonisamide may produce anti-epileptic and anti-convulsant effects through action at both sodium and calcium channels. In vitro pharmacological studies suggest that zonisamide blocks voltage-gated sodium channels and reduces voltage-dependent, transient inward calcium currents (T-type $Ca^{2+}$ currents), consequently stabilizing neuronal membranes and suppressing neuronal hypersynchronization. In vitro binding studies have demonstrated that zonisamide binds to the GABA/benzodiazepine receptor ionophore complex in an allosteric fashion that does not produce changes in chloride flux. Other in vitro studies have demonstrated that zonisamide (10-30 µg/mL) suppresses synaptically-driven electrical activity without affecting postsynaptic GABA or glutamate responses (cultured mouse spinal cord neurons) or neuronal or glial uptake of [$^3$H]-GABA (rat hippocampal slices). Thus, zonisamide does not appear to potentiate the synaptic activity of GABA. In vivo microdialysis studies demonstrated that zonisamide facilitates both dopaminergic and serotonergic neurotransmission.

Murata, et al., (*Neurocsci Res.* 41:397(2001)) report that patients given 50-200 mg/day zonisamide in addition to their anti-Parkinson Disease drug showed lessening of symptoms. Takigawa, et al., (*Rinsho ShinKeigaKa,* 37:1006-9 (1997)) report symptoms of cortical myoclonic tremor of one patient improved after treatment with zonisamide, clonazepam and valpolate. Taira (*NoToShinKei* 44:16-3 (1992)) reports that two patients developed resting and postural hand tremor after administration of zonisamide.

Based on the ability of zonisamide to suppress seizures generated in thalamic regions, Applicants have discovered that zonisamide is efficacious in treating tremors.

SUMMARY OF THE INVENTION

The present invention is directed to a method of treating tremors in a subject in need of such treatment. The method comprises administering to a subject a pharmaceutical composition comprising zonisamide, or a pharmaceutically acceptable salt thereof, in an amount effective to reduce symptoms of tremors. The invention provides a method for treating action tremor such as essential tremor, postural tremor, drug-induced or toxic tremor, primary orthostatic tremor, dystonic tremor, neuropathic tremor, and cerebellar tremor in mammals. The invention also provides a method for treating rest tremor, such as severe essential tremor.

The pharmaceutical composition can be administered in the range of 0.5-10 mg/kg/day through a variety of routes of administration, including oral, topical, rectal, injection, or implantation. A preferred route of administration is via oral dosing.

DETAILED DESCRIPTION OF THE INVENTION

The present invention provides a method of treating subjects afflicted with pathologic tremors, particularly action tremors, which includes postural tremor and kinetic tremor. The present invention is also useful in treating rest tremor such as severe essential tremor. The method comprises administering to a subject a pharmaceutical composition comprising an effective amount of zonisamide, or a pharmaceutically acceptable salt thereof, to reduce symptoms of tremors. A preferred salt is an alkaline metal salt of zonisamide, such as sodium, lithium, potassium, which is stable.

Tremor is defined as an involuntary, rhythmic oscillatory movement of a part or parts of the body, resulting from alternating or irregularly synchronous contractions of antagonist muscles. Tremor is the most common form of involuntary movement. Tremor can be classified according to the clinical phenomenology as rest tremors and action tremors.

Rest tremor is present when skeletal muscles are not voluntarily activated and the relevant body part is fully supported against gravity. Rest tremor may occur with Parkinson's disease, or as hereditary chin quivering, or with severe essential tremor.

Action tremor occurs during voluntary muscle contraction and includes postural and kinetic tremor. Postural tremor is an action tremor that is present while voluntarily maintaining a position against gravity. Postural tremor is often associated with essential tremor or may occur as primary orthostatic tremor, physiologic and enhanced physiological tremors, drug-induced or toxic tremors (including alcohol-related tremors), neuropathic tremor, cerebellar head tremor (titubation) or dystonic tremor.

Kinetic tremor is an action tremor which may occur during any form of voluntary movement including visually- or nonvisually-guided actions, such as speaking, pouring water into a cup, or finger-to-nose testing. Kinetic tremor is often associated with essential tremor, classic cerebellar tremor (e.g., seen in multiple sclerosis, infarction), dystonic tremor, drug-induced or toxic tremors, or midbrain lesions. Kinetic tremor also includes dynamic or terminal tremor, which occurs with target-directed movements, and simple kinetic tremor, which is present with nontarget-directed actions. Task- or position-specific tremor is a kinetic tremor that occurs during performance of highly specialized, complex movements, such as writing, speaking, or smiling. Isometric tremor is a kinetic tremor present during voluntary muscle contraction against a rigid stationary object, such as making a fist or flexing the wrist against a horizontal, flat surface.

The present invention is useful for treating action tremors such as essential tremor, postural tremor, drug-induced or toxic tremor (including alcohol-related tremor), cerebellar tremor, primary orthostatic tremor, dystonic tremor and neuropathic tremor.

Essential tremor is a chronic neurological disorder, and the most common movement disorder. The only symptom of ET is tremor. Other diseases, which may cause tremor, are usually associated with additional symptoms. ET seems to occur most frequently in the hands. It can also affect the head, voice, tongue, arms, legs and trunk. Tremor can occur in more than one body part simultaneously (i.e., hands/head, head/voice, and arms/hands). Individuals with ET often describe a feeling of internal shaking.

Drug-induced and toxic tremor syndromes are induced by pharmacologic agents used to treat other medical conditions. Such medications include theophylline, valproate, lithium, tricyclic antidepressants, neuroleptics, sympathomimetics, amphetamines, steroids, certain agents used to treat endocrine and metabolic disorders, or other miscellaneous agents. Toxic tremor, such as seen in manganese, arsenic, or mercury intoxication or poisoning, occurs in association with other neurologic symptoms, such as gait disturbances, rigidity, dystonia, ataxia, dysarthria, confusion, etc.

Cerebellar tremor syndromes are pure or primary intention tremors with a frequency predominantly less than 5 Hz, possibly in association with postural (but not resting) tremor. Other forms of tremor, such as postural tremor, are deemed of cerebellar origin only when coexistent with other cerebellar signs.

Primary orthostatic tremor is a postural tremor of lower limb, trunk, and, possibly upper limb muscles during stance yet absent when sitting or reclining. In most patients, orthostatic tremor is suppressed upon walking. As seen on EMG, orthostatic tremor is characterized by high frequency, 13 to 18 Hz entrainment of synchronous motor unit activity of contraleteral and ipsilateral muscles, primarily of the lower limbs.

Dystonic tremor refers to primarily postural and kinetic tremor occurring in a body part affected by dystonia. Dystonia is a neurologic movement disorder characterized by sustained muscle contractions that frequently cause repetitive, twisting, or writhing movements and distorted, postures or positions. Dystonic tremor may affect any voluntary muscle in the body. Postural hand tremor commonly affects dystonia patients and is frequently indistinguishable from essential tremor. As with dystonia, gestes antagonistes, such as tapping or stroking of affected or adjacent muscles, may alleviate dystonic tremor by reducing tremor amplitude.

Neuropathic tremor is associated with certain peripheral neuropathies, particularly dysgammaglobulinemic neuropathies. Neuropathic tremor is primarily kinetic and postural tremor of the affected extremities.

Zonisamide has a unique combination of pharmacologic actions: it inhibits voltage-gated sodium channels and also blocks T-type calcium channels. Applicants believe that these mechanisms play a role in tremor modulation, via neuronal stabilization. The pharmacokinetic and drug interaction profiles of zonisamide are ideal for treating tremors in a subject. Zonisamide has the ability to stabilize neuronal membranes and suppress neuronal hyper-sychronization in harmaline-induced tremor model. Harmaline-induced postural/kinetic tremor in animals shares most features with human essential tremor/enhanced physiological tremor due to its olivoerebellar/thalamic involvement. Applicants believe that zonisamide is effective in treating tremors by membrane stabilizing actions in thalamic regions.

The pharmaceutical composition of the present invention can be applied by any of the accepted modes of systemic administration for agents which affect the central nervous system (CNS) including oral, parenteral, rectal, and otherwise systemic routes of administration. Any pharmaceutically acceptable mode of administration can be used, including solid, semi-solid, or liquid dosage forms, such as for example, tablets, suppositories, pills, capsules, powders, liquids suspensions, or the like, preferably in unit dosage form suitable to single administration of precise dosages, or in sustained or controlled release forms for the prolonged administration of the compound at a predetermined rate. The compositions typically include a conventional pharmaceutical carrier or excipient and the drug product zonisamide and, in addition, can include other medicinal agents, pharmaceutical agents, carriers, etc. The compositions are advantageously compounded into unit dosage forms, containing a predetermined, standard amount of the active compound, to make dosing and patient compliance simpler.

The amount of active compound administered depends on the subject being treated, the severity of the affliction, the manner of administration and the judgment of the prescribing physician. However, an effective dosage is in general in the range of 0.5-10 mg/kg/day, preferably 2-10 mg/kg/day which can be administered all at a time or in divided doses. The dosage of these compounds can vary in accordance with the administration route, the age of the patient and the degree of the therapeutic effect desired.

The compounds of the present invention are usually administered in the form of a pharmaceutical composition that contains them in admixture with a pharmaceutical carrier. The pharmaceutical composition can be in the dosage forms such as tablets, capsules, granules, fine granules, powders, syrups, suppositories, injections, or the like. These preparations can be prepared by conventional methods.

The carriers useful for these preparations include all organic or inorganic carrier materials that are usually used for the pharmaceutical preparations and are inert to the active ingredient. Examples of the carriers suitable for the preparation of tablets capsules, granules and fine granules are diluents such as lactose, starch, sucrose, D-mannitol, calcium sulfate, or microcrystalline cellulose; disintegrators such as sodium carboxymethylcellulose, modified starch, or calcium carboxymethylcellulose; binders such as methylcellulose, gelatin, acacia, ethylcellulose, hydroxypropylcellulose, or polyvinylpyrrolidone; lubricants such as light anhydrous silicic acid, magnesium stearate, talc, or hydrogenated oil; or the like. When formed into tablets, they can be coated in a conventional manner by using the conventional coating agents such as calcium phosphate, carnauba wax, hydroxypropyl methylcellulose, macrogol, hydroxypropyl methylphthalate, cellulose acetate phthalate, titanium dioxide, sorbitan fatty acid ester, or the like.

Examples of the carriers suitable for the preparation of syrups are sweetening agents such as sucrose, glucose, fructose, or D-sorbitol; suspending agents such as acacia, tragacanth, sodium carboxymethylcellulose, methylcellulose, sodium alginate, microcrystalline cellulose, or veegum; dispersing agents such as sorbitan fatty acid ester, sodium lauryl sulfate, or polysorbate 80; or the like. When formed into syrups, the conventional flavoring agents, aromatic substances, preservatives, or the like may optionally be added thereto. The syrups may be in the form of dry syrup that is dissolved or suspended before use.

Examples of bases used for the preparation of suppositories are cacao butter, glycerin saturated fatty acid ester, glycerogelatin, macrogol, or the like. When formed into suppositories, the conventional surface active agents, preservatives or the like can optionally be admixed.

When formed into injections, the alkali metal salt of the compound is dissolved in distilled water for injection, to which may optionally be added the conventional solubilizers, buffering or pH adjusting agents, isotonic agents, preservatives and other suitable substances. The injections can be in the solid dry preparations, which are dissolved before use.

These pharmaceutical compositions usually contain zonisamide as the active ingredient in an amount of 0.5% by weight or more, preferably 10 to 70% by weight, based on the total weight of the composition. These compositions can optionally contain other therapeutically active compounds.

For solid compositions, conventional non-toxic carriers may be used, which includes, mannitol, lactose, starch, magnesium stearate, sodium saccharin, talcum, cellulose, glucose, sucrose, magnesium carbonate, and other like substances. The active compound as defined above may be formulated as suppositories using, for example, polyalkylene glycols, for example, propylene glycol as a carrier. Liquid pharmaceutically administerable compositions can, for example, be prepared by dissolving, dispersing, etc. an active compound as defined above and optional pharmaceutical adjuvants in a carrier, such as, for example, water, saline, aqueous dextrose, glycerol, ethanol, and the like to thereby form a solution or suspension. If desired, the pharmaceutical composition to be administered can also contain minor amounts of non-toxic auxiliary pH buffering agents and the like, for example, sodium acetate, sorbitan monolaurate, triethanolamine oleate, etc. Actual methods of preparing such dosage forms are known, or will be apparent to those skilled in this art; for example, see Remington's Pharmaceutical Sciences, Mack Publishing Company, Easton, Pa., 15th Edition, 1975. The composition or formulation to be administered contains a quantity of the active compound in an amount effective to alleviate the symptoms of the subject being treated.

Dosage forms or compositions containing active ingredient in the range of 0.25 to 95% with the balance made up from non-toxic carrier may be prepared. For oral administration, a pharmaceutically acceptable non-toxic composition is formed by the incorporation of any of the normally employed excipients, and contains 1-95%, preferably 5-50%, of the active ingredient.

Parenteral administration is generally characterized by injection, whether intravenously, subcutaneously, intramuscularly, or perineurally. Injectables can be prepared in conventional forms, either as liquid solutions, suspensions, or emulsions. Suitable excipients include, for example, water, saline, aqueous dextrose, glycerol, ethanol or the like. In addition, the pharmaceutical compositions can also contain minor amounts of non-toxic substances such as wetting or emulsifying agents, auxiliary pH buffering agents and the like, such as, sodium acetate, sorbitan monolaurate, triethanolamine oleate, etc. A preferred injectable is a sterile solution comprising zonisamide sodium.

The percentage of active compound contained in such parenteral compositions is highly dependent on the specific nature thereof, as well as the activity of the compound and the needs of the subject. However, percentages of active ingredient in solution are in general 0.1 to 10%, and preferably 0.2-2%.

Other modes of administration can also be practiced in accordance with the present invention.

For delayed release, the compounds of the invention can be formulated in a pharmaceutical composition, such as in microcapsules formed from biocompatible polymers, or in liposomal carrier systems according to methods known in the art.

For continuous release of active agent, the compound can be covalently conjugated to a water soluble polymer, such as a polylactide or biodegradable hydrogel derived from an amphipathic block copolymer, as described in U.S. Pat. No. 5,320,840. Collagen-based matrix implants, such as described in U.S. Pat. No. 5,024,841, are also useful for sustained delivery of therapeutics.

The method of the present invention can be used with other therapeutic agents commonly used to treat tremor, thus enhancing the effects of therapeutic agents and adjunctive treatment. Other therapeutic agents used include beta-blocker propranolol, timolol, benzodiazapine (alprazolam, clonazepam, diazepam, lorazepam), anti-depressant (trazadone, mirtazapine), centrally acting alpha-agonist (clonidine), anti-apsamodic (botulinum toxin injection), anti-seizure (gabapentin, primidone, phenobarbital) and non-competitive NMDA channel blocker (MK-801). Other treatments include surgical treatments.

High doses are sometimes required for some therapeutic agents to achieve levels to effectuate the target response, but high doses are often associated with a greater frequency of dose-related adverse effects. Thus, combined use of the pharmaceutical composition of the present invention with therapeutic agents commonly used to treat tremor allows the use of relatively lower doses of other agents, which results in a lower frequency of adverse side effects associated with long-term administration of such agents. Thus, another advantage of the compound in this invention is to reduce adverse side effects of other drugs used to treat tremor. These adverse effects may include tolerance, dependence, constipation, respiratory depression, sedation, and gastrointestinal side effects.

The following examples further illustrate the present invention. These examples are intended merely to be illustrative of the present invention and are not to be construed as being limiting.

EXAMPLES

The purpose of the study of Examples 1-4 is to evaluate the potential efficacy of zonisamide on essential tremor in an established, harmaline-induced, rodent model of tremor. Animal models of tremor have been widely used in experimental neurology, because they are an indispensable requirement for understanding the pathophysiology of human tremor disorders and the development of new therapeutic agents (Wilms, et al., *Mov. Disord.* 14:557-71 (1999)).

Example 1

Materials and Methods for Evaluating Zonisamide in Rodent Model

Test Animals

Adult Sprague-Dawley female rats (Harlan Sprague Dawley, Inc., CA) at approximately 200-250 grams of body weight are used in this experiment. Animals are allowed free access to water and commercial rodent diet under standard laboratory conditions. The room temperature is maintained at 20-23° C. and illumination is on a 12/12-hour light dark cycle.

Based upon the design of the experiment, a total of sixty animals are used in the experiment (Tables 1, 2).

Drug Preparation

All solutions are prepared fresh for each day of experimental trial. The dose preparation procedures for the zonisamide are provided by the Sponsor.

Tremorigenic Agent

Harmaline (Sigma) is the most widely used experimental tremor-inducing agent, and numerous studies have been published using this agent in rodent model. Studies suggest that an olivocerebello-bulbospinal pathway mediates harmaline-induced tremor, which resembles essential tremor in humans. The severity of harmaline-induced tremor is dose dependent and the effective dose range is 10 to 50 mg/kg delivered intraperitoneally, (Biary, et al., *Pharmacology, Biochemistry & Behavior*, 65:117, (2000), Cross et al., *Psychopharmacology*, 111:96-98 (1993)).

The harmaline solution is prepared by dissolving this agent in saline. A preliminary pilot study determines a preferred way to administer harmaline (intraperitoneally or subcutaneously) to produce a long-lasting 8-12 Hz tremor.

Experimental Treatment Agent

Zonisamide (sodium salt) is provided by Elan Pharmaceuticals. Studies with zonisamide have previously established that an oral dose of 20 mg/kg in rats was effective in anticonvulsant models (Misuno, et al., *Nihon Shinkei Seishin YaKurigaKu Zasshi*, 17:17-23 (1997)). Doses selected for testing in the harmaline model are 20 and 50 mg/kg per os (po, by mouth) Zonisamide sodium is dissolved in sterile water to produce a dosing solution of 20 mg/ml. Doses of 20 and 50 mg/kg are delivered by oral gavage.

Positive Control Agent

In general clinical practices, propranolol has a proven efficacy in ET and has been established as a first line therapy (Koller, et al., *Neurology*, 54:530-38, (2000)).

Propanolol hydrochloride is dissolved in water to produce 20 and 50 mg/ml dosing preparations. Based on published data regarding the use of propranolol in animal models, propranolol is administered at 20 and 50 mg/kg via oral gavage (Suemaru, et al., *Naunyn Schmiedebergs Arch Pharmacol.*, 355:571-5 (1997); Wishart and Herberger, *Pharmacol. Biochem Behav.* 11:625-9 (1979)).

Example 2

Harmaline-Induced Pilot Study

A prolonged harmaline tremor is needed in order to clearly see the effect of the zonsisamide. Subcutaneous harmaline injections give a prolonged response to drugs in general, and are suitable for the zonisamide study. This pilot study determines an effective dose/delivery of harmaline that produces a prolonged 8-12 Hz tremor, ideally lasting at least three hours. Five animals are given 10 mg/kg i.p., or 10 mg/kg s.c. of harmaline (see Table 1). The successful dose/delivery is determined based on the following criteria: 80% or more of all the test animals, per each harmaline-dosing group, have tremor activity at 8-12 Hz lasting for at least 3 hours.

All animals are treated as described in Table 1.

TABLE 1

Harmaline Pilot Study

| Group | Harmaline Dose | Dose Volume (ml/kg) | Number of Animals |
|---|---|---|---|
| 1 | 10 mg/kg., i.p. | 1 ml/kg | 5 |
| 2 | 10 mg/kg, s.c. | 1 ml/kg | 5 |

Harmaline Pilot Study Protocol:
1) Place rat in tremor cage for 10 min.
2) Record activity for 20 min. (baseline)
3) Inject harmaline (10 mg/kg) i.p. or s.c.
4) Wait 2 minutes
5) Place rat in tremor cage, wait 10 minutes for harmaline to take effect.
6) Record tremor for 6 hours.

Example 3

Effects of Harmaline on Inducing Tremor

Six female Sprague-Dawley rats were treated with i.p. saline and placed in a tremor monitoring cage for 30 minutes of baseline recording. They then received 10 mg/kg harmaline i.p. to induce tremor. Recording of the harmaline-induced tremor began 15 minutes after the harmaline injection and continued for up to 2½ hours.

A transducer connected to the cage floor recorded motion, which was processed by Fourier transform and spectral analysis. Motion at 8-12 Hz (the range in which the tremor occurs) was compared to the full spectrum of motion recorded (0-15 Hz). The results show that the effect of harmaline on inducing tremor in rates was stable for over two hours.

Example 4

Zonisamide Study

In this experiment, the efficacy of zonisamide to reduce tremor in the harmaline-induced tremogenic rodent model is evaluated. The efficacy of zonisamide is compared to the leading anti-tremor therapy agent, propranolol (positive control) as well as a vehicle, sterile water (negative control). All animals are treated with 10 mg/kg harmaline to achieve the tremorigenic behavior. All treatment agents are administered via oral gavage.

To analyze the reduction of tremor caused by treatment agents, a Convuls-1 pressure sensitive transducer system is used. Convuls-1 is designed to objectively quantify convulsive or tremorous activity in small laboratory animals. An unrestrained animal is placed within a chamber that resides upon a sensing platform. The platform is connected to a load sensor that converts the vertical component of motion into an electrical signal. The instrument accumulates impulse counts over time. An impulse count is accrued for each gram-second (980 dynes) of force applied to the sensing platform. Convuls-1 responds only to changes in the force exerted on the platform. The static force exerted by the weight of the platform and animal is not recorded. The combined weight of the animal, platform and any additional caging does, however, limit the maximum observable force. Convuls-1 has a maximum force sensing range of 2 kg. The addition of the forces exerted by the static elements, subtracted from the four pound maximum, yields the usable sensing range of the complete system. Convuls-1 is equipped with two sensing ranges: gram-seconds and 100 milligram-seconds. Output power is recorded digitally and analyzed for change of frequency and power using the Dataware A/D converted and software.

The data is analyzed in one minute bins. For each bin, the total power of 0-15 Hz and the total power at 8-12 Hz is calculated. The data is then converted into Excel and the ratio of 8-12 Hz/0-15 Hz power is calculated. In control rats, this ratio is 15-30%. In harmaline-treated rats, this ratio is typically 60-80%. This ratio is the final outcome measure. Normally 20 or more minutes of data are collected for each condition to give a proper ratio because of minute-to-minute variability.

All animals are treated as described in Table 2.

TABLE 2

Zonisamide Study

| Group | Treatment | Number of Animals | Dose (mg/kg) | Route | Dosing Solution Conc (mg/ml) | Dose Volume (mL/kg) |
|---|---|---|---|---|---|---|
| 1 | Zonisamide | 10 | 20 | po | 20 | 1 |
| 2 | Zonisamide | 10 | 50 | po | 20 | 2.5 |
| 3 | Propranolol | 10 | 20 | po | 20 | 1 |
| 4 | Propranolol | 10 | 50 | po | 20 | 2.5 |
| 5 | Water | 10 | 0 | po | 0 | 2.5 |

At the end of the experiment animals are sacrificed using halothane and decapitation.

Zonisamide Study Protocol:
1) Fast rat for 4-8 hours.
2) Place rat in tremor cage for 10 min.
3) Record tremor activity for 20 min. (baseline).
4) Inject 10 mg/kg harmaline.
5) Wait 2 minutes.
6) Place in tremor cage, wait for 10 minutes for harmaline to take effect.
7) Record tremor 20 minutes.
8) Administer test article (zonisamide, propanolol, or water) via oral gavage.
9) Wait 2 minutes.
10) Place back in tremor cage for 10 minutes.
11) Record for 4-6 hours.
Statistical analysis.
Data is analyzed by a repeated measures ANOVA followed by Fisher's LSD.

Example 5

Zonisamide was used in treatment of patients at an outpatient neurology clinic, which provided the following results. Adverse reactions experienced in treatment were GI upset, somnolence and skin rash. Kidney stones and anhydrosis (lack of sweating) were not encountered in the patients treated. For intractable essential tremor, 10 patients (age range: 46 to 82) were identified who were either intolerant to, or failed on, primidone or propranolol therapy. The dosage of zonisamide to these patients was 100 mg to a maximum of 200 mg once daily. The study dose was continued for at least 12 weeks unless discontinued earlier due to side effects. Of the ten patients, who did not respond to other treatment, four patients responded by reduction in tremor of greater than 50% and reported a better quality of life. Amongst other categories: mixed tremor (non-essential, secondary to trauma or multiple sclerosis), two out of two patients responded; multi-infarct-related (2 or more minor strokes) tremor, one out of two patients responded; and in Parkinsonian tremor, two out of four responded.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude the specification.

What is claimed is:

1. A method of treating essential tremor in a subject in need thereof comprising administering to the subject a therapeutically effective amount of a pharmaceutical composition comprising zonisamide or a pharmaceutically acceptable salt thereof.

2. The method of claim 1, wherein the essential tremor is severe essential tremor.

3. The method of claim 1, wherein the therapeutically effective amount is in the range of about 0.5 mg/kg/day to about 10 mg/kg/day.

4. The method of claim 1, wherein the pharmaceutical composition is administered orally to the subject.

5. The method of claim 1, wherein the pharmaceutical composition is administered parenterally to the subject.

6. The method of claim 5, wherein the pharmaceutical composition is a sterile solution comprising zonisamide sodium.

7. The method of claim 5, wherein the pharmaceutical composition is administered intravenously, subcutaneously, or intramuscularly.

8. The method of claim 1, further comprising administering another therapeutic agent used to treat essential tremor.

9. The method of claim 1, further comprising administering propranolol, timolol, alprazolam, clonazepam, diazepam, lorazepam, trazadone, mirtazapine, clonidine, a botulinum toxin injection, gabapentin, primidone, phemobarbital or MK-801.

10. A method for treating severe essential tremor in the rest state in a subject in need thereof comprising administering to the subject a therapeutically effective amount of a pharmaceutical composition comprising zonisamide or a pharmaceutically acceptable salt thereof.

11. The method of claim 10, wherein the therapeutically effective amount is in the range of about 0.5 mg/kg/day to about 10 mg/kg/day.

12. The method of claim 10, wherein the pharmaceutical composition is administered orally to the subject.

13. The method of claim 10, wherein the pharmaceutical composition is administered parenterally to the subject.

14. The method of claim 13, wherein the pharmaceutical composition is a sterile solution comprising zonisamide sodium.

15. The method of claim 13, wherein the pharmaceutical composition is administered intravenously, subcutaneously, or intramuscularly.

16. The method of claim 13, further comprising administering another therapeutic agent used to treat severer essential tremor in the rest state.

17. The method of claim 10, further comprising administering propranolol, timolol, alprazolam, clonazepam, diazepam, lorazepam, trazadone, mirtazapine, clonidine, a botulinum toxin injection, gabapentin, primidone, phemobarbital or MK-801.

18. A method for treating action tremor in a subject in need thereof comprising administering to the subject a therapeutically effective amount of a pharmaceutical composition comprising zonisamide or a pharmaceutically acceptable salt thereof.

19. The method of claim 18, wherein the action tremor is postural tremor.

20. The method of claim 18, wherein the action tremor is drug-induced or toxic tremor; primary orthostatic tremor; dystonic tremor; or neuropathic tremor.

21. The method of claim 18, wherein the action tremor is cerebellar tremor.

22. The method of claim 18, wherein the therapeutically effective amount is in the range of about 0.5 mg/kg/day to about 10 mg/kg/day.

23. The method of claim 18, wherein the pharmaceutical composition is administered orally or parenterally to the subject.

24. A method for treating kinetic tremor in a subject in need thereof comprising administering to the subject a therapeutically effective amount of a pharmaceutical composition comprising zonisamide or a pharmaceutically acceptable salt thereof.

* * * * *